United States Patent
Swane

(10) Patent No.: US 11,801,159 B2
(45) Date of Patent: Oct. 31, 2023

(54) APPLICATOR FOR COLD TREATMENT

(71) Applicant: TheOTCLab Holding B.V., Amsterdam (NL)

(72) Inventor: Albert Swane, Amsterdam (NL)

(73) Assignee: THEOTCLAB HOLDING B.V., Amsterdam (NL)

( * ) Notice: Subject to any disclaimer, the term of this patent is extended or adjusted under 35 U.S.C. 154(b) by 204 days.

(21) Appl. No.: 17/368,913

(22) Filed: Jul. 7, 2021

(65) Prior Publication Data
US 2022/0008245 A1 Jan. 13, 2022

(30) Foreign Application Priority Data

Jul. 9, 2020 (EP) .................................... 20185027

(51) Int. Cl.
*A61F 7/00* (2006.01)

(52) U.S. Cl.
CPC ........ *A61F 7/00* (2013.01); *A61F 2007/0052* (2013.01); *A61F 2007/0068* (2013.01); *A61F 2007/0087* (2013.01)

(58) Field of Classification Search
CPC ... A61B 2018/00982; A61F 2007/0052; A61F 2007/0068; A61F 2007/0087; A61F 2007/0093; A61F 2007/0095; A61F 7/00; A61F 7/08
See application file for complete search history.

(56) References Cited

U.S. PATENT DOCUMENTS

2015/0359664 A1* 12/2015 Herweijer ............. A61F 7/0085
604/290
2020/0129221 A1 4/2020 De Naeyer et al.

FOREIGN PATENT DOCUMENTS

| EP | 1065980 A1 * | 1/2001 | ......... A61B 18/0218 |
| EP | 1065980 A1 | 1/2001 | |
| WO | 2014114696 A1 | 7/2014 | |

OTHER PUBLICATIONS

Extended European Search Report for corresponding European application No. 20185027.8, dated Dec. 16, 2020 (8 pages).

* cited by examiner

*Primary Examiner* — Tigist S Demie
(74) *Attorney, Agent, or Firm* — Mendelsohn Dunleavy, P.C.

(57) ABSTRACT

Applicator (3) for cold treatment, comprising an applicator housing (5) with an inlet opening (18) and a leak tight tip (23). The applicator housing (5) encloses a channel body (20) extending between the inlet opening (18) and the leak tight tip (23). The applicator (3) is mounted or mountable in a releasable manner onto a pressurized dispenser (2) comprising a nozzle (7), such that the inlet opening (18) is in fluid communication with the nozzle (7). The applicator housing (5) is moveable between a rest position and a pressed position to activate the nozzle (7). The applicator housing (5) has release openings (26) which are closed in the pressed position.

19 Claims, 6 Drawing Sheets

APPLICATOR FOR COLD TREATMENT

Figure 1:
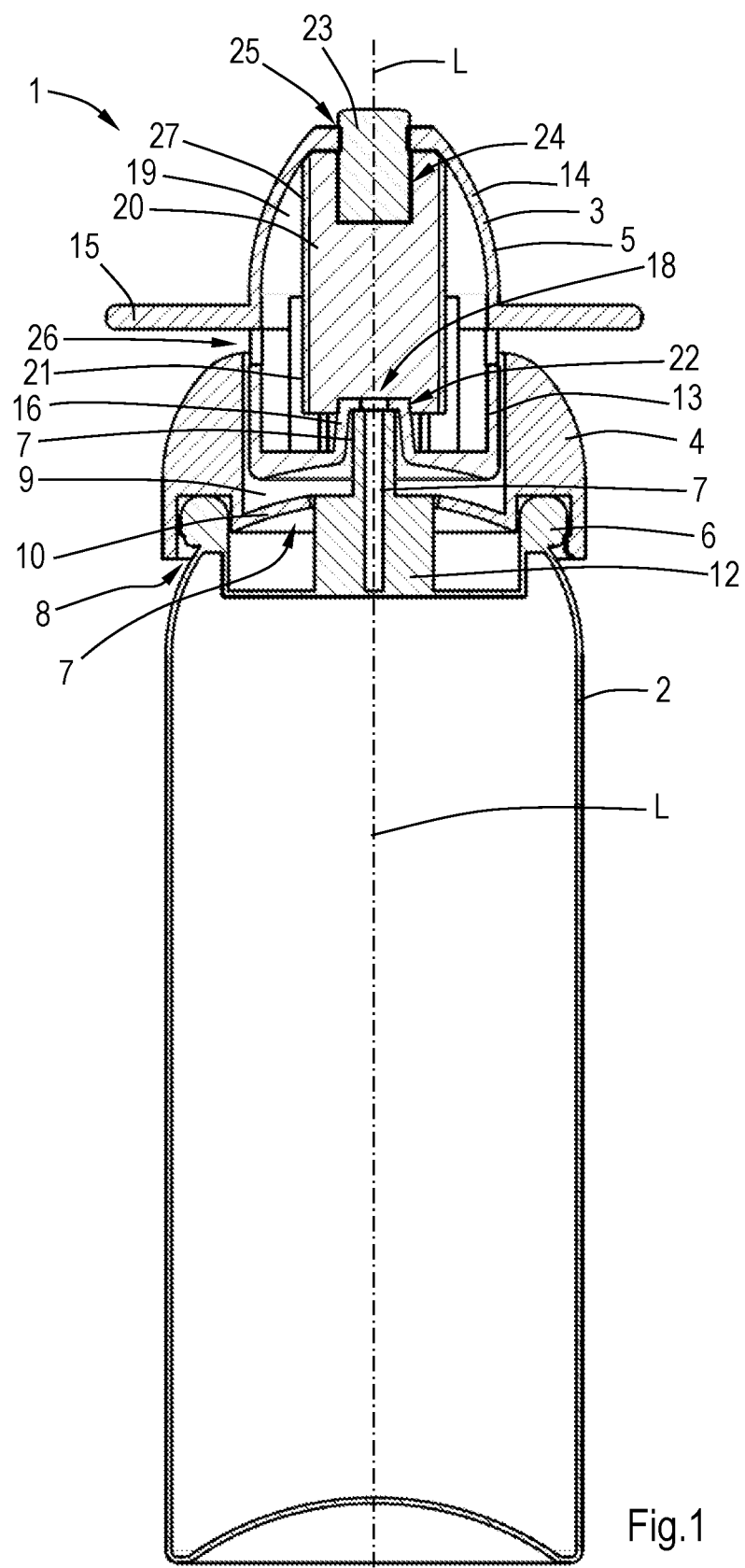

The invention relates to an applicator for cold treatment, e.g., of skin disorders, such as warts, age spots, tick bites, skintags, etc., the applicator being mountable on a pressurized dispenser with a nozzle, the applicator having a leak tight tip for contacting a spot to be treated, the tip being cooled by refrigerant released from the nozzle.

WO 2014/114696 discloses a device for cold treatment of warts comprising an pressurized dispenser and an applicator mounted on the pressurized dispenser. The applicator comprises a closed contact face. By pressing down the applicator, a liquid refrigerant is released from the pressurized dispenser. The refrigerant evaporates in the applicator housing. This extracts heat from the contact face of the applicator. Direct contact between the skin and the liquid refrigerant can result in injury of the skin and needs to be prevented.

The object of the present invention is to provide a system with reduced risk of leakage or spilling of refrigerant liquid.

The object of the invention is achieved with an applicator comprising an applicator housing with an inlet opening and a leak tight tip, the applicator housing enclosing a channel body extending between the inlet opening and the leak tight tip;
 the applicator being mounted or mountable in a releasable manner onto a top end of a pressurized dispenser comprising a nozzle, such that the inlet opening is in fluid communication with the nozzle, the mounted applicator housing being moveable between a rest position and a pressed position to activate the nozzle;
 the applicator housing having one or more release openings which are closed in the pressed position.

This causes a time gap between activation of the nozzle and the cooling effect. The cooling effect is delayed until the release openings are opened. In the pressed position, the one or more release openings are closed, so in this position the refrigerant cannot significantly evaporate and extract heat. Only after the one or more release openings are at least partly opened, e.g., by moving the applicator from the pressed position, the release openings allow the refrigerant to expand and evaporate. As a result, cooling takes place only after moving the applicator from the pressed position. The applicator can be separated from the pressurized dispenser for the desired treatment. The pressurized dispenser can be kept away from the skin to be treated, so the risk of spillage and skin injuries is substantially reduced.

In a specific embodiment, the applicator further comprises a coupler with a lower side mountable or mounted to the pressurized dispenser, and an upper side provided with a coupler recess;
 wherein the applicator housing and the coupler recess have matching outlines enabling movement of the applicator housing within the coupler recess between the rest position and the pressed position;
 wherein the coupler recess has a bottom with a nozzle passage opening in line with the inlet opening in the applicator housing.

After mounting the applicator on the dispenser, the nozzle projects through the nozzle passage opening and connects to the inlet opening.

The applicator housing can easily be separated from the coupler and the pressurized dispenser. The release openings can be positioned in parts of the applicator housing received in the coupler recess when the applicator is in the pressed position, so the coupler recess closes the release openings in that position.

In a particular embodiment, the channel body comprises capillary channels extending between the nozzle engaging end and the leak tight tip. Capillary channels are channels which are too small to allow evaporation of the refrigerant liquid. This helps to delay the cooling effect. The combination of surface tension, caused by cohesion within the liquid, and adhesive forces between the liquid and channel wall, generates a capillary action preventing evaporation and propelling the liquid to the tip of the channel body. The capillary channels may for example have a largest diameter of at most 100 pm, e., at most 75 pm, e.g., at least 20 pm.

The channel body can for example be formed of a thermally insulating material, such as a plastic material, such as capillary foam, e.g., of a capillary polyester foam. The channel body can for example be made of a highlighter felt material, in particular of a highlighter felt polyester. Such material comprises a high density of straight and parallel capillary channels, allowing fast transport of refrigerant liquid towards the leak tight tip.

The cooling effect increases with the length of the channel body. Hence, the length of the channel body can be selected on basis of the desired cooling effect for treatment of a certain skin disorder.

In a further embodiment, the side wall or side walls of the channel body can be sealed by a liner, preventing refrigerant from escaping via the side wall. Particularly preferred is a channel body of highlighter felt material with a side wall or side walls sealed by a liner, and with top and bottom faces without the liner, the capillary channels running between the top and bottom faces.

The leak tight tip provides a contact surface for contacting a spot to be treated. The leak tight tip will typically be of a heat conductive material, e.g., having a thermal conductivity of at least 10 $Wm^{-1}K^{-1}$. Suitable materials are for instance metals, in particular stainless steel, titanium, aluminum or alloys thereof. The tip is leak tight, meaning that the refrigerant liquid cannot permeate through the tip and cannot leak between the tip and the adjacent sections of the applicator housing.

In a specific embodiment, the applicator housing of the applicator has walls spaced from the channel body. This helps to define a suitable flow path towards release openings in the walls of the applicator housing. The spacing between the walls and the channel body is for example at most 3, 5 mm.

Optionally, the bottom of the applicator housing comprises an inwardly protruding part of the bottom comprising the inlet opening and spacing a bottom face of the channel body from the bottom of the applicator housing, so the bottom of the channel body is not completely blocked by the bottom of the applicator housing.

In a specific embodiment, the tip is formed by an insert partly received in a recess of the top end of the channel body and an opening of the applicator housing in line with the recess in the channel body.

The insert may for example be a metal insert or an insert of a material impregnated with a therapeutically active ingredient.

In a specific embodiment, the applicator housing can comprise a slit which can elastically be forced, e.g., by pinching or pressing, to move from a closed rest position to an open position. In the closed position the leak tight tip is covered and in the open position the leak tight tip is exposed and ready for use. Such an embodiment is particularly useful for the treatment of skin tags or tick bites. First, the applicator housing is pressed down, as described above. Then, while the applicator housing is removed from the pressurized dispenser, the refrigerant escapes and the delayed cooling effect starts. The slit is then forced apart and put on the skin tag or biting tick. The slit is then released and pinches the skin tag or biting tick while the treated disorder is cooled by the cooled tip.

The invention also pertains to an assembly of an applicator and a matching pressurized dispenser containing a refrigerant liquid. The pressurized dispenser can for example be of the standard type aerosol container or spray can having a top end with a circumferential seam joint around the nozzle. This seam joint can be used for a snap connection with a matching circumferential recess at the lower end of the coupler.

The present disclosure also pertains to an applicator comprising an applicator housing with an inlet opening and a leak tight tip, the applicator housing enclosing a capillary channel body as described above, with capillary channels extending between the inlet opening and the leak tight tip; the applicator being mounted or mountable in a releasable manner onto a top end of an pressurized dispenser comprising a nozzle, such that the inlet opening is in fluid communication with the nozzle, the mounted applicator housing being moveable between a rest position and a pressed position to activate the nozzle.

Moreover, the present disclosure also pertains to an applicator for cold treatment, optionally comprising any one of the features as disclosed above, comprising an applicator housing with an inlet opening and a leak tight tip, wherein the applicator housing comprises a slit which can elastically be forced to move from a closed rest position, covering the leak tight tip, to an open position, exposing the leak tight tip.

The applicator of the present invention can for example be used for the treatment of skin disorders, such as warts, age spots, skin tags, burns, insect bites, rings or bags under the eyes, bruises or swellings.

A single dispenser can be combined with interchangeable applicators having different tips for different skin disorders. Similarly, when the dispenser is empty, it can easily be replaced by a filled one, without disposing the applicator.

Suitable refrigerant liquids include volatile hydrocarbons, such as methyl ether, dimethyl ether, liquid hydrofluoroolefins, n-butane, isobutane or propane. Nitrous oxide and carbon dioxide can also be used.

The invention will be further explained with references to the accompanying drawings, showing exemplary embodiments.

Figure 2:
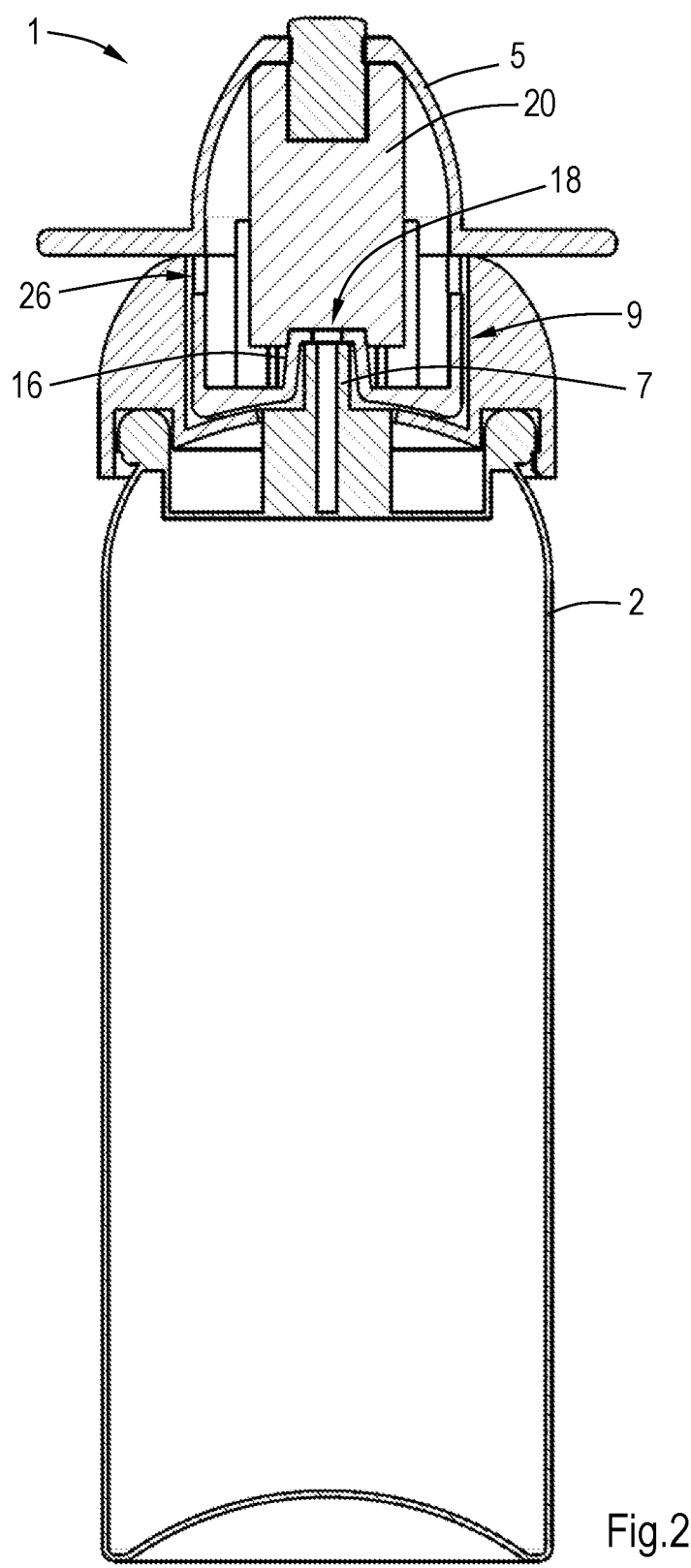
Figure 3:
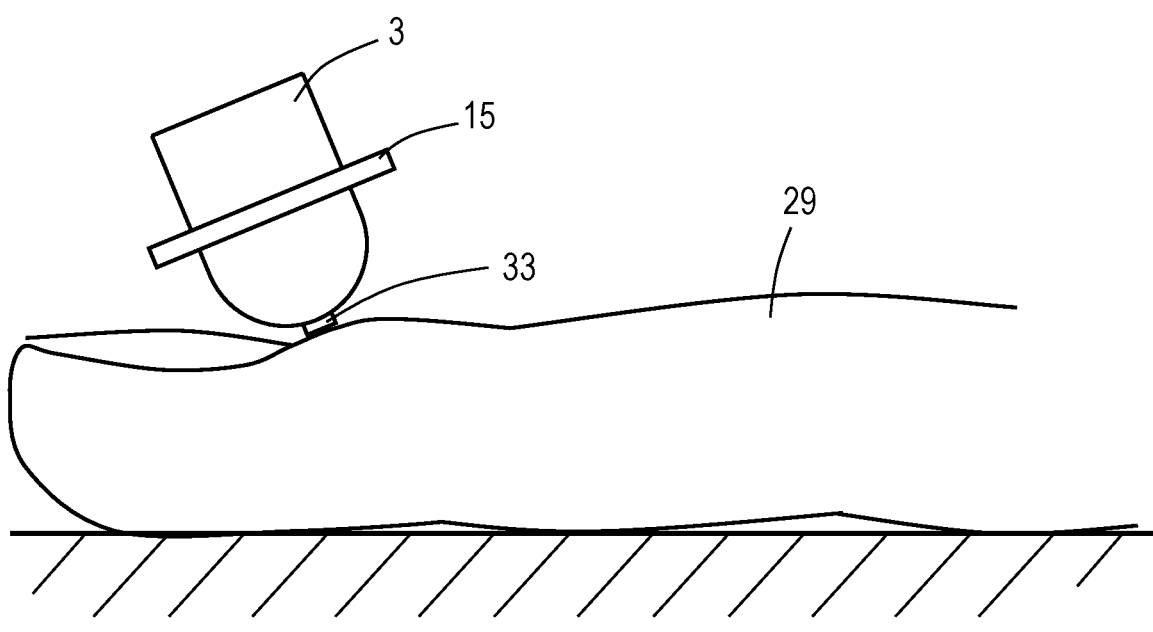
Figure 4:
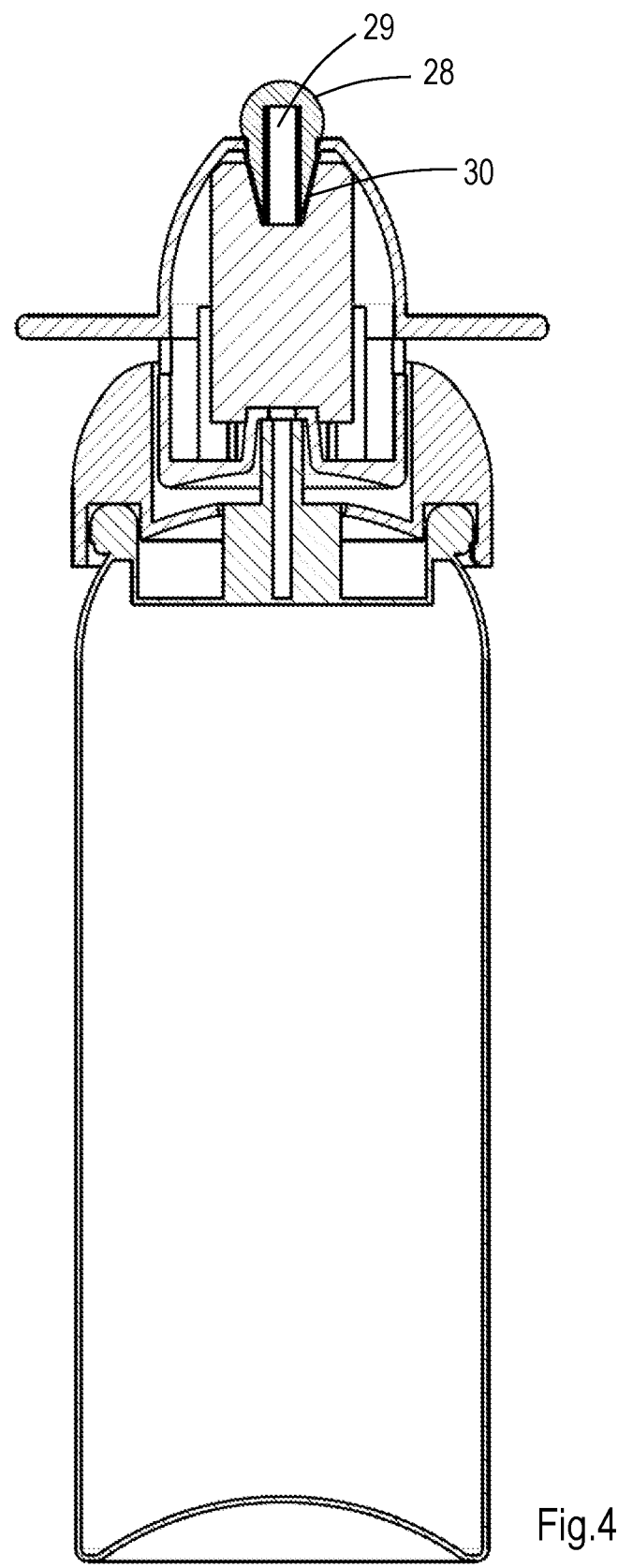
Figure 5:
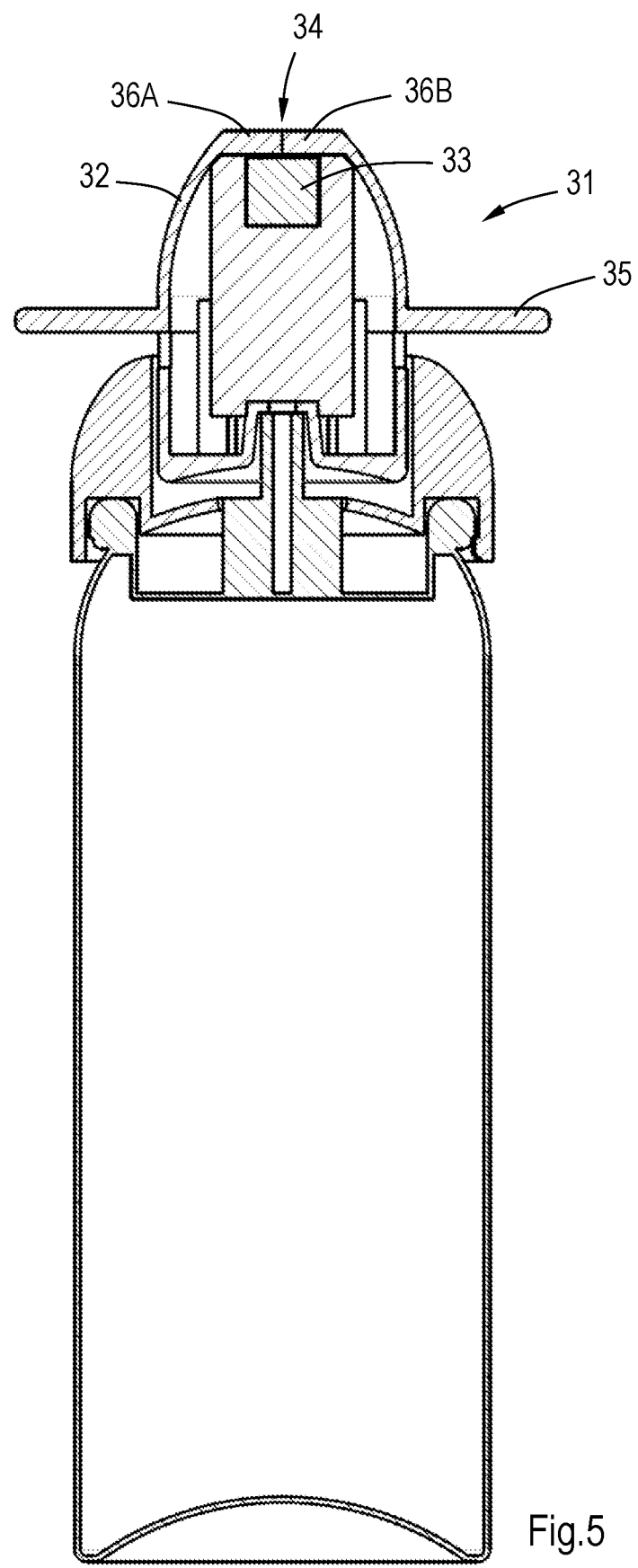
Figure 6:
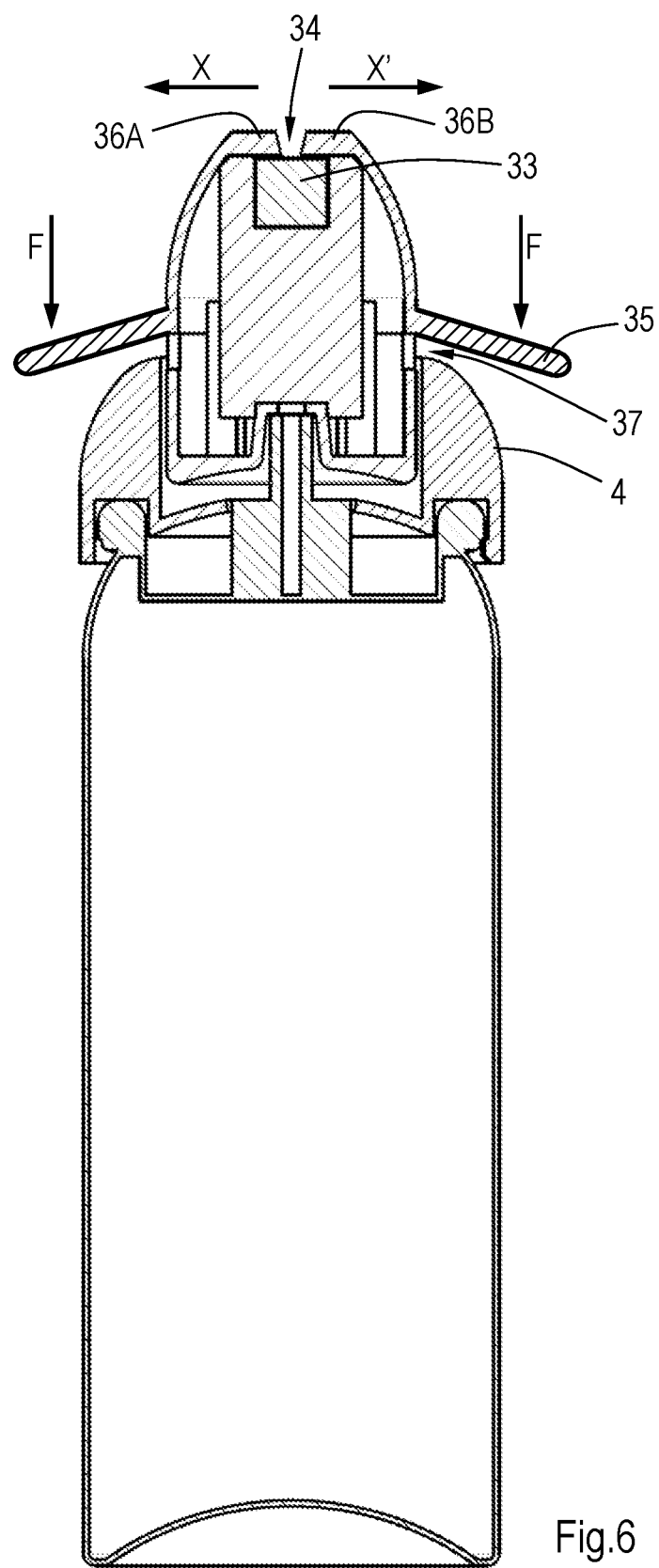

FIG. 1: shows a first exemplary embodiment of an assembly of a dispenser with an applicator in cross section;

FIG. 2: shows the assembly of FIG. 1 with the applicator in a pressed down position;

FIG. 3: shows the applicator of FIG. 1 during treatment;

FIG. 4: shows a second exemplary embodiment;

FIG. 5: shows a third exemplary embodiment;

FIG. 6: shows the embodiment of FIG. 5 when activated.

FIG. 1 shows an assembly 1 of a pressurized dispenser 2 and an applicator 3 for cold treatment. The applicator 3 comprises a coupler 4 and an applicator housing 5. The assembly 1 is shown in cross section and is essentially cylindrically symmetrical about its longitudinal axis L.

The pressurized dispenser 2 is shaped as a standard aerosol container with a top end having a circumferential seam joint 6 around a nozzle 7. The pressurized dispenser 2 contains a refrigerant liquid. Pressing down the nozzle 7 releases the refrigerant liquid from the pressurized dispenser 2 via the nozzle 7.

The coupler 4 has a lower end with a circumferential recess 8 forming a releasable snap fit or clamp fit connection with the seam joint 6 of the pressurized dispenser 2.

The coupler 4 has an upper end provided with a coupler recess 9 receiving the applicator housing 5. The coupler recess 9 and the applicator housing 5 have matching cylindrical outlines so the applicator housing 5 fits within the coupler recess 9 and can be freely slid up and down within the coupler recess 9. Other outlines can also be used as long as the applicator housing 5 fits within the coupler recess 9 only allowing movement guided by the shape of the coupler recess 9, e.g., a sliding fit allowing sliding movement in a direction parallel to the longitudinal axis L of the assembly 1.

The coupler recess 9 has a bottom 10 with a central nozzle passage opening 11. The nozzle 7 of the pressurized dispenser 2 projects through the nozzle passage opening 11. The bottom of the coupler recess 9 is substantially flush with an upper face of a base 12 of the nozzle 7.

The applicator housing 5 has a cylindrical lower end 13 fitting within the coupler recess 9, and a substantially conical truncated top end 14. Between the top end 14 and the lower end 13, the applicator housing 5 has two oppositely extending flanges 15 providing grip for a user and allowing the user to push down the applicator housing 5.

The lower end 13 of the applicator housing 5 has a bottom with an inwardly protruding cylindrical part 16 receiving a tip 17 of the nozzle 7. This protruding part 16 is provided with a central inlet opening 18 aligned with the nozzle tip 17.

The applicator housing 5 has an interior space 19 enclosing a channel body 20. The channel body 20 extends between the protruding bottom part 16 and the top end of the applicator housing 5. A set of fins 21 extending upward from the bottom of the applicator housing 5, serve to lock the channel body 20 in place.

The channel body 20 is wider than the protruding bottom part 16. As a result, the lower end of the channel body 20 protrudes from all sides with respect to the protruding bottom part 16. The lower end of the channel body 20 comprises a section 22 in fluid communication with the nozzle 7. In this exemplary embodiment, the section 22 is formed by a recess receiving the outer tip of the protruding bottom part 16.

The channel body 20 is cylindrical or it may have any other suitable outline. The channel body 20 is made of a highlighter felt polyester. This is a foamy material with numerous capillary channels extending in a direction substantially parallel to the longitudinal axis of the assembly, i.e., from the nozzle to the top end of the applicator housing 5. The cylindrical side wall of the channel body is sealed by a liner 27, which is substantially impermeable for refrigerant liquid and refrigerant vapour. Due to the liner 27 any refrigerant liquid can only flow via the bottom section of the channel body 20.

The truncated top end 14 of the applicator housing 5 is provided with a leak tight tip 23 of a thermally conductive material, in particular stainless steel, chromated copper or a similar metal. This tip 23 is formed by an insert partly received in a matching recess 24 at the top side of the channel body 20 and protruding through a matching opening 25 in the truncated top end of the applicator housing 5. Any gap between the opening 25 and the insert 24 is sealed to prevent any leakage of refrigerant liquid.

The wall of the applicator housing 5 has a number of release openings 26 just below the flanges 15. The walls of the applicator housing 5 are spaced from the channel body 20. Also the bottom 10 of the applicator housing 5 is spaced from the channel body 20, except where the channel body 20 is supported by the inward protruding bottom part 16, so as to create a direct flow path from the bottom of the channel body 20 to the release openings 26.

FIG. 1 shows the assembly 1 with the applicator housing 5 in a rest position, with the applicator housing 5 passively resting on top of the nozzle 7 of the pressurized dispenser 2. In this position, the release openings 26 are not closed and the interior spacing of the applicator housing 5 is in open communication with the ambient air via the release openings 26.

From this position, the user can push down the applicator housing 5 into a pressed position, as shown in FIG. 2. In this position, the release openings 26 are fully closed by the wall of the coupler recess 9 and the nozzle 7 of the pressurized dispenser 2 is pressed down. Liquid refrigerant is dispensed from the nozzle 7 via the inlet opening 18 in the protruding bottom part 16 into the capillary channels of the channel body 20. The capillary channels are too small to allow evaporation of the refrigerant liquid. Part of the liquid will escape via the bottom of the channel body 20 to the interior space 19 of the applicator housing 5 but as long as the applicator housing 5 is in the pressed position, refrigerant vapour cannot escape through the release openings 26. Pressure will build up in the applicator housing interior 19 and a saturated vapour pressure develops, resulting from an equilibrium of refrigerant vapour and liquid. Hence, in the pressed position evaporation of refrigerant liquid in the applicator 3 is negligible and too little to create a substantial cooling effect.

The user can then lift the applicator housing 5. The nozzle 7 stops dispensing the refrigerant liquid from the pressurized dispenser 2. The release openings 26 are opened allowing refrigerant vapour to escape. Liquid refrigerant in the applicator housing 5 is now free to evaporate and extracts heat from the thermally conductive leak tight tip 23. The user can simply remove the applicator housing 5 from the coupler 4 and treat the skin disorder with the cooled leak tight tip 23, while keeping distance from the pressurized dispenser 2, as shown in FIG. 3, which shows treatment of a disorder on a person's finger 29. The relatively small applicator housing 5 is easy to handle compared to prior art applicator heads which remain coupled to the dispenser during treatment.

The metal insert 23 as shown in FIG. 1 is particularly useful for the treatment of warts. For other skin disorders it may be useful to combine the cold treatment with topical application of a therapeutically active agent. In that case, other types of tips may be used. An example of an alternative embodiment with an alternative tip is shown in FIG. 4. This tip 28 is particularly suitable for the treatment of verruca. The tip 28 is made of a relatively soft, compressible absorbing material with an interior reservoir 29 filled with a therapeutically active substance, e.g., an acid. At the face contacting the channel body the tip is sealed by a liner 30 which is impermeable for the liquid refrigerant.

Other alternative tips include a cross shaped tip for the treatment of insect bites or a spreadable tip for skin tags.

FIG. 5 shows an embodiment of an assembly 31 of the same construction as the embodiment of FIG. 1, except that it has an applicator housing 32 with a tip 33 fully covered by the top wall of the housing. The top wall of the applicator housing 32 is provided with a longitudinal slit 34, separating wall parts 36A, 36B. By pinching the applicator housing 32, or by applying a pressing force F on the two flanges 35, the wall parts 36A, 36B are spread apart and are forced to move elastically in opposite directions X, X' in order to expose the cooled tip 33, as shown in FIG. 6. After the applicator housing is removed from the coupler 4, the refrigerant is allowed to escape via the release openings 37 to trigger the cooling effect, and the opened slit 35 can be positioned on a skin tag or a biting tick or the like. Subsequently, the flanges 35 are released, allowing the slit 34 to close and pinch the skin tag or tick. Meanwhile the cooled tip 33 cools the treated disorder.

The invention claimed is:

1. Applicator for cold treatment, comprising an applicator housing with an inlet opening and a leak tight tip, the applicator housing enclosing a channel body extending between the inlet opening and the leak tight tip;
   the applicator being mounted or mountable in a releasable manner onto a pressurized dispenser comprising a nozzle, such that the inlet opening is in fluid communication with the nozzle, the applicator housing being moveable between a rest position and a pressed position to activate the nozzle;
   characterized in that the applicator housing has one or more release openings which are closed in the pressed position; and
   a coupler with a lower side mountable or mounted to the pressurized dispenser, and an upper side provided with a coupler recess;
   wherein the applicator housing and the coupler recess have matching outlines enabling movement of the applicator housing within the coupler recess between the rest position and the pressed position; and
   the coupler recess has a bottom with a nozzle passage opening in line with the inlet opening in the applicator housing.

2. The applicator according to claim 1, wherein the channel body comprises capillary channels extending between the inlet opening of the applicator housing and the leak tight tip.

3. The applicator according to claim 2, wherein the channel body is made of a capillary foam.

4. The applicator according to claim 3, wherein the channel body has side walls sealed by a liner.

5. The applicator according to claim 3, wherein the channel body is made of a highlighter felt polyester.

6. The applicator according to claim 2, wherein the channel body has side walls sealed by a liner.

7. The applicator according to claim 1, wherein the applicator housing has walls spaced from the channel body.

8. The applicator according to claim 1, wherein a bottom of the applicator housing comprises an inwardly protruding bottom part defining the inlet opening and spacing a bottom face of the channel body from the bottom of the applicator housing.

9. The applicator according to claim 1, wherein the tip is formed by an insert partly received in a recess of a top end of the channel body and an opening of the applicator housing in line with the recess.

10. The applicator according to claim 9, the insert being a metal insert or an insert of a material impregnated with a therapeutically active ingredient.

11. The applicator according to claim 1, wherein the applicator housing comprises a slit which is configured to be elastically moved between a closed position and an open position exposing the leak tight tip.

12. Assembly of the applicator according to claim 1 and the matching pressurized dispenser containing a refrigerant liquid.

13. Assembly according to claim 12, wherein the pressurized dispenser comprises a circumferential seam joint forming a snap connection with a matching circumferential recess of the applicator.

14. The assembly according to claim 12, wherein a snap condition is formed at a bottom side of the coupler.

15. The applicator according to claim 1, wherein the channel body comprises capillary channels extending between the inlet opening of the applicator housing and the leak tight tip.

16. The applicator according to claim 1, wherein the applicator housing has walls spaced from the channel body.

17. The applicator according to claim 1, wherein a bottom of the applicator housing comprises an inwardly protruding bottom part defining the inlet opening and spacing a bottom face of the channel body from the bottom of the applicator housing.

18. The applicator according to claim 1, wherein the tip is formed by an insert partly received in a recess of the top end of the channel body and an opening of the applicator housing in line with the recess.

19. The applicator according to claim 1, wherein the applicator housing comprises a slit which is configured to be elastically moved between a closed position and an open position exposing the leak tight tip.

\* \* \* \* \*